(12) United States Patent
Herzog

(10) Patent No.: US 6,579,700 B1
(45) Date of Patent: Jun. 17, 2003

(54) NPY FAMILY MEMBER

(75) Inventor: Herbert Herzog, New South Wales (AU)

(73) Assignee: Garvan Institute of Medical Research, Darlinghurst (AU)

( * ) Notice: Subject to any disclaimer, the term of this patent is extended or adjusted under 35 U.S.C. 154(b) by 0 days.

(21) Appl. No.: 09/529,727

(22) PCT Filed: Oct. 15, 1998

(86) PCT No.: PCT/AU98/00864

§ 371 (c)(1),
(2), (4) Date: Sep. 1, 2000

(87) PCT Pub. No.: WO99/19351

PCT Pub. Date: Apr. 22, 1999

(30) Foreign Application Priority Data

Oct. 15, 1997 (AU) .............................. PO 9813

(51) Int. Cl.⁷ ........................ A61K 38/10; A61K 38/17; C07H 21/04; C12N 15/63; C12N 5/10
(52) U.S. Cl. .................. 435/69.1; 435/320.1; 435/325; 514/2; 514/12; 514/14; 530/300; 530/326; 536/23.1
(58) Field of Search .............................. 435/69.1, 320.1, 435/325; 514/2, 12, 14; 530/326, 300; 536/23.1

(56) References Cited

PUBLICATIONS

Anders Blomqvist and Herbert Herzog, "Y–receptor sub-types—how many more?," Review, *Trends in NeuroScience*, 20(7):294–298 (1997).

Herbert Herzog, et al., "Seminalplasmin: Recent evolution of another member of the neuropeptide Y gene family," Genetics, *Proc. Natl. Acad. Sci. USA*, 92:594–598 (Jan. 1995).

Yvonne Hort, et al., "Gene Duplication of the Human Peptide YY Gene (PYY) Generated the Pancreatic Polypeptide Gene (PPY) on Chromosome 17q21.1," *Genomics*, 26:77–83 (1995).

Dan Larhammar, "Evolution of neuropeptide Y, peptide YY and pancreatic polypeptide," *Regulatory Peptides*, 62:1–11 (1996).

Andrew Leiter, "Peptide YY—Structure of the Precursor and Expression in Exocrine Pancreas," *J. Biol. Chem.*, 262(27):12984–12988 (1987).

Ian Taylor, et al., "Pancreatic Polypeptide—Metabolism and Effect on Pancreatic Secretion in Dogs," *Gastroenterology*, 76:524–528 (1979).

*Primary Examiner*—Gary Kunz
*Assistant Examiner*—Stephen Gucker
(74) *Attorney, Agent, or Firm*—Marshall, Gerstein & Borun

(57) ABSTRACT

The present invention relates to isolated polynucleotides encoding novel PY peptides, and to isolated PY peptides and functionally equivalent fragments thereof. The PY peptides of the present invention may be useful in regulating central and peripheral nervous and endocrine systems.

17 Claims, 2 Drawing Sheets

Human PY cDNA

```
                                                                   70
      *         *         *         *         *         *         *
CCAGTGCGCCCTTGAAACTTTCCTCGCCTTCCACCTCCTGCTCATCTGCTTCACAAGCTGTCGCTGTGGT
                                                                  140
      *         *         *         *         *         *         *
GTCGGTTCGCAGGTCGTGGCCTCTCATGGCCACGGTGCTTTTGGCCCTGCTCGTCTACCTGGGGGCGCTG
                                 M  A  T  V  L  L  A  L  L  V  Y  L  G  A  L>
                                                                  210
      *         *         *         *         *         *         *
GTCGACGCCTACCCCATCAAACCCGAGGCTCCCGGCGAAGACGCCTTCCTGGGGTAGCTGAGCCGCTGCT
 V  D  A  Y  P  I  K  P  E  A  P  G  E  D  A  F  L  G>
                                                                  280
      *         *         *         *         *         *         *
ACGCCTATCCTCGCCACTACCTCATCCTGGTCACTCAGCCGTCGTGAGCGCAGGCGCGGGGCGGGCGGAC
                                                                  350
      *         *         *         *         *         *         *
GGGGACCCCTGGGGCTCTCCCCCTACAGCCCCGCTCCACCGGGGGCGTGGCTAGATCTGACCGCGCCCGG
                                                                  420
      *         *         *         *         *         *         *
CCAGGCCCCGCCCTCAGGTATGGGAAACTAGGCCGCCCAGTCGCGCGCCTCTCCAAAACGTTCTTCCCAG
                                                                  490
      *         *         *         *         *         *         *
ACTGCGAGGACCGCCTCGGCAGGTGGCGGTAAAAGCGCCCCCATCAAGTCACATAACATCCTGCCTCCGA
                                                                  560
      *         *         *         *         *         *         *
GAGCGCGGTCTGGCCCCACCCTGGTCCATCATCACTTACGACGTCTCCCAGGCTTGCCTCCCCGGATCGG
                                                                  630
      *         *         *         *         *         *         *
ATTCCTTTCCCTTCGATCCCGCAGGCCGGAGGGCGCAGACCTGTGGTGAGGACACCCGAGGCCTCCTGGG
                                                                  700
      *         *         *         *         *         *         *
AGACCTGCAGACCACGCCCACCTCATTTACATGTTCACTCCCGACCCTGGAAACCCGGATTTCGCCTCCG
                                                                  770
      *         *         *         *         *         *         *
GACAGCGGCGTCTGGGCAGGGTTCGGGTACTGCAGTCCCGCGTCTGGATGCCCCGCGCCCCCTGAGCTGC
                                                                  840
      *         *         *         *         *         *         *
AGGGCTGTGTGTGGTCCTTCCCTGGTCCCAAAATAAAGAGCGGATTGCACAGAAACGGAAAAAAAAAAA
```

FIG. 1

Baboon PY gene

```
                                                                      70
         *         *         *         *         *         *         *
TCCTTGAAACTTTCCTCGCCTTCTACCTCCTGCTCATCTGCTTCATAAGCTGTCGCTGTGAGCGGCTGGG
                                                                     140
         *         *         *         *         *         *         *
GGCTCAAGCATGGTCTGGTACCAGGAAATCCAGGCTGTTTTGTCGGGAAACTAAGGCTGGAATGGTGGAA
                                                                     210
         *         *         *         *         *         *         *
GCTCGGGGTAAGTGGTGGGGAACTGGATTCGACGGGGTCATTGGAGGTGGGAACGAGGCCCGGGACTCCC
                                                                     280
         *         *         *         *         *         *         *
CGGGAGTCCCCGTTGCCAGCACAACCCTCTTCTCTAATTTACCTCTCTGGCAGCAGCGGTGCCGGGGCGG
                                                                     350
         *         *         *         *         *         *         *
TTTATGTCAGGCAGGGCTTATGTCCCTCTGACAGATTAGGAAACTGAGGCAGGAGCCGGTGCAGTGCCGG
                                                                     420
         *         *         *         *         *         *         *
AGAACACACGGCAAGTTGGTTGCTGAACCTTGATCCGCTACCAGCCTCAGGGAGAGGGCCGGAGCCCGGC
                                                                     490
         *         *         *         *         *         *         *
CAGAGGGCAGCCGCAGCCTCCTGCCGTGGAGGATCGAGGCTCGGAACGACCCACACCCCAACGTCACCTT
                                                                     560
         *         *         *         *         *         *         *
CCCAGATGGTGTCGGTGCGCAGGTCGTGGCCTACCATGGCCACAGTGCTTTTGGCCCTGCTCGTCTACCT
     M  V  S  V  R  R  S  W  P  T  M  A  T  V  L  L  A  L  L  V  Y  L>
                                                                     630
         *         *         *         *         *         *         *
GGGGGCGCTGGTCGAGGCCCACCCCATCAAACCCGAGGCTCCAGGCGAAGACGCCCCCCTGGAGGAGCTG
     G  A  L  V  E  A  H  P  I  K  P  E  A  P  G  E  D  A  P  L  E  E  L>
                                                                     700
         *         *         *         *         *         *         *
AGCCTCTACTACGCCTCCCTGAGCCACTACCTCAACCTGGTCACCCGGCCGTGGTGAGCGCAGGCGCGGG
     S  L  Y  Y  A  S  L  S  H  Y  L  N  L  V  T  R  P  W>
                                                                     770
         *         *         *         *         *         *         *
GTGGGCCGAGCGGGACCCCTGGGGCTCTCCCGCTGCGGCCCCTCTCCACCGGGGGCGTGGTCAGATTTGA
                                                                     840
         *         *         *         *         *         *         *
CCACGCCCTTCCAGGCCCCACCCCCAGGCATGGGAGGACAGCCCGGACACACGCCTCTCCAAAACGTTCT
                                                                     910
         *         *         *         *         *         *         *
TCCCAGACGGCGAGGACCGCCCGGGCAGGTCACAGTAAAAGCGCCCCCGTCAAGTCACATAACATCCTGC
                                                                     980
         *         *         *         *         *         *         *
CTCCGAGAGTGCGGCCTGGCCCCACCCTGGTACATCACTTACGACGTCTCCCAGGCTCGCCTCCCCAGAT
                                                                    1050
         *         *         *         *         *         *         *
CGGATTCCTTTCCCTTCACTCCCGCAGGCTGGAGGCGCAGACCTGTGGTGAGGACCCCCGAGGCCTCCTG
         *         *         *         *         *         *         *
GGAGATCTGCAGACCACGCCCACCTCATTTACATGTTCACTCCCAATCACTAGTGAATTC
```

FIG. 2

NPY FAMILY MEMBER

CROSS REFERENCE TO RELATED APPLICATIONS

This is the US National Phase of PCT/AU98/00864 filed Oct. 15, 1998 and from which priority is claimed under 35 USC §119.

FIELD OF THE INVENTION

The present invention relates to isolated polynucleotides encoding PY peptides. The present invention also relates to isolated PY peptides and functionally equivalent fragments thereof, and to methods of treatment involving administration of these peptides.

BACKGROUND OF THE INVENTION

The neuropeptide Y (NPY) gene family, which also includes peptide YY (PYR) and pancreatic polypeptide (PP), is an example of multiple gene duplication events giving rise to a range of structurally related but functionally distinct gene products (1). NPY is one of the most highly conserved peptides known (for example, with only three amino acid differences between human and shark NPY), suggesting that this peptide subserves evolutionary old and important functions. In the mammalian nervous system, NPY is one of the most abundant neuropeptides and acts both centrally and peripherally to regulate the cardiovascular system. It also modulates a wide range of other important physiological activities, including appetite, central endocrine secretion, anxiety, and reproduction (2). On the other hand, PYY is secreted from endocrine cells in the lower small intestine, colon, and pancreas. It acts in an inhibitory nature on the gastrointestinal tract, including inhibition of gastric acid secretion, gastric emptying, pancreatic exocrine secretion, and gut motility (3). The third member of the NPY family, PP, is secreted by cells within the endocrine and exocrine pancreas and specifically inhibits the section of enzymes and bicarbonate from the exocrine pancreas (4).

Analysis of the structure and localization of the genes encoding NPY, PYY and PP has suggested that these genes arose from an initial gene duplication event that generated the NPY and PYY genes, followed by a subsequent duplication of the PYY gene to create the PP gene. The human NPY gene has been mapped to chromosome 7, while the PYY and PP genes lie only 10 kb apart on chromosome 17q21.1 (5). Consistent with this evolution by gene duplication, all three genes share a common intron/exon structure, although the three introns of the NPY gene (in all species studied to date) are much larger than the corresponding introns in the PYY and PP genes. The overall nucleotide sequence similarity between the three members of the gene family is restricted to the coding regions and ranges from approximately 55% (NPY vs. PYY) to 38% (NPY vs. PP) and 30% (PY vs. PP).

SUMMARY OF THE INVENTION

The present inventors have now identified a novel member of the NPY gene family. This gene, designated PY, appears to be expressed in a range of tissue types including lung, kidney, liver, ovary, adrenal gland, heart, pancreas, testis and brain. This pattern of expression is consistent with other members of the NPY gene family and suggests that the PY peptide plays an important role in central and peripheral nervous and endocrine systems.

Accordingly, in a first aspect the present invention provides an isolated polynucleotide encoding a PY peptide or a functionally equivalent fragment thereof.

The term "isolated polynucleotide" is intended to refer to one or both of the following: a polynucleotide not immediately contiguous with both of the coding sequences with which it is immediately contiguous (i.e., one at the 5' end and one at the 3' end) in the naturally-occurring genome of the organism from which the polynucleotide is derived; or a polynucleotide which is substantially free of a nucleic acid with which it occurs in the organism from which the polynucleotide is derived.

In one preferred embodiment the isolated polynucleotide encodes a human pre-pro PY peptide of about 33 amino acids or a mature amidated peptide of about 14 amino acids or a non-amidated peptide of 15 amino acids.

In another preferred embodiment the isolated polynucleotide encodes a baboon pre-pro PY peptide of about 63 amino acids or a mature peptide of about 35 amino acids.

More preferably, the isolated polynucleotide encodes a human PY peptide including an amino acid sequence substantially corresponding to amino acids 19 to 33 in SEQ ID NO:2 or a baboon PY peptide having a sequence substantially corresponding to amino acids 29 to 63 in SEQ ID NO;4.

In a further preferred aspect, the polynucleotide includes
(a) a sequence of nucleotides as shown in SEQ ID NO:1 or SEQ ID NO:3 or a functional equivalent thereof;
(b) a sequence complementary to the sequence of paragraph (a); or
(c) a sequence which selectively hybridises to a sequence in paragraph (a) or paragraph (b).

In a preferred embodiment, the sequence defined in paragraph (c) hybridises to a sequence in paragraph (a) or paragraph (b) under stringent conditions.

When used herein, "high stringency" refers to conditions that (i) employ low ionic strength and high temperature for washing after hybridization, for example, 0.1×SSC and 0.1% (w/v) SDS at 50° C.; (ii) employ during hybridization conditions such that the hybridization temperature is, 25° C. lower than the duplex melting temperature of the hybridizing polynucleotides, for example 1.5×SSPE, 10% (w/v) polyethylene glycol 6000, 7% (w/v) SDS, 0.25 mg/ml fragmented herring sperm DNA at 65° C.; or (iii) for example, 0.5M sodium phosphate, pH 7.2, 5 mM EDTA, 7% (w/v) SDS (28) and 0.5% (w/v) BLOTTO at 70° C.; or (iv) employ during hybridizational denaturing agent such as formamide, for example, 50% (v/v) formamide with 5×SSC, 50 mM sodium phosphate (pH 6.5) and 5×Denhardt's solution at 42° C.; or (v) employ, for example, 50% (v/v) formamide, 5×SSC, 50 mM sodium phosphate (pH 6.8), 0.1% (w/v) sodium pyrophosphate, 5×Denhardt's solution, sonicated salmon sperm DNA (50 μg/ml) and 10%. dextran sulphate at 42° C.

In a preferred embodiment, the polynucleotide is less than 5000 nucleotides in length, more preferably less than 2000 nucleotides in length, more preferably less than 1000 nucleotides in length and more preferably less than 500 nucleotides in length.

In a preferred embodiment the polynucleotide defined in paragraph (a) includes a sequence characterised by nucleotides 150 to 194 of SEQ ID NO:1 or nucleotides 580 to 684 of SEQ ID NO:3 or a functional equivalent of either of these sequences.

By "functional equivalent" we mean a sequence which differs from the sequence defined in SEQ ID NO:1 or SEQ ID NO:3 but which, through the degeneracy of the genetic code, encodes a polypeptide substantially as shown in SEQ ID NO:2 or SEQ ID NO:4.

In a further preferred embodiment, the polynucleotides of the present invention share at least 50% homology, more preferably at least 70% homology, more preferably at least 80% homology, more preferably at least 90% homology and more preferably at least 95% homology with a sequence shown in SEQ ID NO:1 or SEQ ID NO:3 wherein the homology is calculated by the BLAST program blastn as described in Altschul. S. F., Madden, T. L. Schaffer. A. A. Zhang. J., Zhang, Z., Miller, W. And Lipman. D. J. (1997) "Gapped BLAST and PSI-BLAST: a new generation of protein database search programs", Nucleic Acids Research 25(171:3389–3402.

The polynucleotide of the present invention may comprise DNA or RNA sequences.

The isolated polynucleotide may be incorporated into plasmids or expression vectors (including viral vectors), which may then be introduced into suitable bacterial, yeast, insect and mammalian host cells. Such host cells may be used to express the PY peptide encoded by the isolated polynucleotide molecule.

Accordingly, in a second aspect, the present invention provides a mammalian, insect, yeast or bacterial host cell transformed with the polynucleotide of the first aspect.

In a third aspect, the present invention provides a method of producing PY peptides or functionally equivalent fragments thereof, comprising culturing the host cell of the second aspect under conditions enabling the expression of the polynucleotide molecule and optionally recovering the PY peptide or fragments thereof.

The terms peptides, proteins, and polypeptides are used interchangeably herein.

Preferably, the host cell is of bacterial, yeast, mammalian or insect origin. Where the cell is mammalian, it is presently preferred that it be a Chinese hamster ovary (CHO) cell, human embryonic kidney 293 cell or human VAtT 20 cell. Where the cell is of insect origin, it is presently preferred that it be an insect Sf9 cell.

The polynucleotides of the present invention encode a member of the NPY peptide family which may be of interest both clinically and commercially as it is expressed in many regions of the body and the NPY family of peptides is known to affect a wide number of systems.

By using the polynucleotides of the present invention it is possible to obtain isolated PY peptides or fragments thereof. By "isolated peptide" we mean a peptide that has been separated from other peptides, lipids and nucleic acids with which it naturally occurs.

The peptide sequence shown in SEQ ED NO:2 is a human pre-pro-protein of 33 amino acids of which the first 18 amino acids represents the signal sequence and the remaining 15 amino acids represent the mature PY peptide.

The peptide sequence shown in SEQ ID NO:4 is a baboon pre-pro-protein of 63 amino acids of which the first 28 amino acids represents the signal sequence and the remaining 35 amino acids represent the mature PY peptide.

Accordingly, in a fourth aspect, the present invention provides an isolated PY peptide including an amino acid sequence characterised by amino acids 19 to 33 in SEQ ID NO:2 or amino acids 29 to 63 in SEQ ID NO:4 or a mutant, allelic variant, species homologue or a biologically active fragment thereof.

In a preferred embodiment of the fourth aspect, the an isolated PY peptide includes an amino acid sequence as shown in SEQ ID NO:2 or SEQ ID NO:4.

In a fifth aspect the present invention provides a polynucleotide encoding a polypeptide according to the fourth aspect.

By "allelic variant" we mean (i) a variant of the sequence defined SEQ ID NO:2 which occurs naturally in humans and which encodes a PY protein; or (ii) a variant of the sequence defined SEQ ID NO:4 which occurs naturally in baboons and which encodes a PY protein.

By "species homologue" we mean the equivalent polynucleotide or protein which occurs naturally in another species, and which performs the equivalent function in that species to the polynucleotide of SEQ ID NO:2 or SEQ ID NO:4.

It will be appreciated that "mutants" of the PY peptide may be produced which exhibit altered activity and that these mutants may be therapeutically useful.

Such mutants may be naturally occurring mutants which may arise within an individual or a population by virtue of point mutation(s), deletion(s) or insertion(s) of DNA sequences, by recombination, gene conversion, flawed replication or rearrangement. Alternatively, such mutants may be produced artificially, for example by site-directed mutagenesis, by "gene shuffling", by deletion using exonuclease(s) and/or endonuclease(s), or by the addition of DNA sequences by ligating portions of DNA together, or by the addition of DNA sequences by template-dependent and/or template-independent DNA polymerase(s).

Thus, the polynucleotide of the fifth aspect may be a mutant such as a dominant negative mutant which encodes a gene product causing an altered phenotype by, for example, reducing or enhancing the activity of endogenous PY.

In a preferred embodiment, the mutant retains the ability to interact with a PY receptor.

In a preferred embodiment, the mutant, allelic variant or species homologue shares at least 50% homology, more preferably at least 70% homology, more preferably at least 80% homology, more preferably at least 90% homology and more preferably at least 95% homology with a sequence shown in SEQ ID NO:2 or SEQ ID NO:4 wherein the homology is calculated by the BLAST program blastx as described in Altschul, S. F., Madden, T. L., Schaffer, A. A., Zhang, J., Zhang, Z., Miller, W. And Lipman, D. J. (1997) "Gapped BLAST and PSI-BLAST; a new generation of protein database search programs", Nucleic Acids Research 25(17):3389–3402.

By "biologically active fragment" we mean a fragment of a sequence shown in SEQ ID NO:2 or SEQ ID NO:4 which retains at least one of the activities of a native PY peptide which activities include the ability to mimic the binding of a native PY peptide to at least one antibody or ligand molecule.

It will be appreciated by those skilled in the art that a number of modifications may be made to the polypeptides and fragments of the present invention without deleteriously affecting the biological activity of the polypeptides or fragments. This may be achieved by various changes, such as sulfation, phosphorylation, nitration and halogenation; or by amino acid insertions, deletions and substitutions, either conservative or non-conservative (eg. D-amino acids, desamino acids) in the peptide sequence where such changes do not substantially alter the overall biological activity of the peptide. Preferred substitutions are those which are conservative, i.e., wherein a residue is replaced by another of the same general type. As is well understood, naturally-occurring amino acids can be subclassified as acidic, basic, neutral and polar, or neutral and nonpolar. Furthermore, three of the encoded amino acids are aromatic. It is generally preferred that encoded peptides differing from the determined polypeptide contain substituted codons for amino acids which are from the same group as that of the amino acid replaced. Thus, in general, the basic amino acids Lys, Arg, and His are interchangeable; the acidic amino acids Asp and Glu are interchangeable; the neutral polar amino acids Ser, Thr, Cys, Gln, and Asn are interchangeable; the non-polar aliphatic amino acids Gly, Ala, Val, Ile, and Leu are conservative with respect to each other (but because of size, Gly and Ala are more closely related and Val, Ile and Leu are more closely related), and the aromatic amino acids Phe, Trp and Tyr are interchangeable.

It should further be noted that if polypeptides are made synthetically, substitutions by amino acids which are not naturally encoded by DNA may also be made. For example, alternative residues include the omega amino acids of the formula $NH_2(CH_2)_nCOOH$ wherein n is 2–6. These are neutral, nonpolar amino acids, as are sarcosine, t-butyl alanine, t-butyl glycine, N-methyl isoleucine, and norleucine. Phenylglycine may substitute for Trp, Tyr or Phe; citrulline and methionine sulfoxide are neutral nonpolar, cysteic acid is acidic, and ornithine is basic. Proline may be substituted with hydroxyproline and retain the conformation conferring properties.

In a sixth aspect, the present invention provides an antibody capable of specifically binding to a PY peptide according to the fourth aspect of the present invention.

The term "antibody" should be construed as covering any specific binding substance having a binding domain with the required specificity. Thus, the term covers antibody fragments, derivatives, functional equivalents and homologues of antibodies, including any polypeptide including an immunoglobulin binding domain, whether natural or synthetic. Chimaeric molecules including an immunoglobulin binding domain, or equivalent, fused to another polypeptide are therefore included.

In a seventh aspect the present invention provides a pharmaceutical composition including an antibody according to the sixth aspect and a pharmaceutically acceptable carrier or diluent.

In an eighth aspect, the present invention provides a non-human animal transformed with a polynucleotide molecule according to the first aspect of the present invention.

In a ninth aspect, the present invention provides an oligonucleotide probe or primer of at least 8 nucleotides, the oligonucleotide having a sequence that hybridizes to a polynucleotide of the first aspect In a preferred embodiment the oligonucleotide is at least 10, more preferably at least 15 and more preferably at least 18 nucleotides in length.

It will be appreciated that the probes or primers of the present invention may be produced by in vitro or in vivo synthesis. Methods of in vitro probe synthesis include organic chemical synthesis processes or enzymatically mediated synthesis, e.g. by means of SP6 RNA polymerase and a plasmid containing a polynucleotide sequence according to the first aspect of the present invention under transcriptional control of an SP6 specific promoter.

In a further preferred embodiment the oligonucleotide probe is conjugated with a label such as a radioisotope, an enzyme, biotin, a fluorescer or a chemiluminescer.

In a tenth aspect, the present invention provides an antisense nucleic acid molecule comprising a nucleotide sequence capable of specifically hybridizing to an MRNA molecule which encodes a PY peptide so as to prevent translation of the mRNA molecule. Such antisense nucleic acid molecules may include a ribozyme region to inactivate catalytically mRNA to which it is hybridized.

In an eleventh aspect the present invention provides a composition comprising a PY peptide according to the present invention and a pharmaceutically acceptable carrier.

Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For example, formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the polypeptide to blood components or one or more organs.

In a twelfth aspect the present invention provides a method of regulating a physiological function selected from blood pressure, anxiety, memory retention, hormone release, conditions related to inflammation, rhinitis, respiratory diseases, conditions related to increased sympathetic nerve activity, sleep disorders and food intake, which method includes administering to a subject a PY peptide according to the present invention.

In a thirteenth aspect the present invention provides the use of a PY peptide according to the present invention in the preparation of a medicament for the treatment of condition selected from blood pressure, anxiety, memory retention, hormone release, conditions related to inflammation, rhinitis, respiratory diseases, conditions related to increased sympathetic nerve activity, sleep disorders and food intake.

The terms "comprise", "comprises" and "comprising" as used throughout the specification are intended to refer to the inclusion of a stated component or feature or group of components or features with or without the inclusion of a further component or feature or group of components or features.

The present invention will now be described, by way of example only, with reference to the following non-limiting Figure and Example.

BRIEF DESCRIPTION OF THE FIGURES

FIG. 1 provides the cDNA sequence (SEQ ID NO:1) and corresponding amino acid sequences (SEQ ID NO:2) of the human PY gene.

FIG. 2 provides the genomic DNA sequence (SEQ ID NO:3) and corresponding amino acid sequences (SEQ ID NO:4) of the baboon PY gene.

EXAMPLE

A human P1 clone containing the entire gene for hPY has been isolated by screening with a $^{32}P$ labelled fragment originated from the human EST clone AA98675. The human gene covers an area of approximately 1.0 Kb and contains one intron. The human PY gene encodes a pre-pro-protein of 33 amino acids of which 18 amino acids represent the signal sequence and the rest the active peptide showing 96% identity to the human PYY gene. The last residue (Gly) is most likely converted into an amide function.

The baboon PY genomic sequence was isolated using degenerate probes based on the human sequence and standard PCR technology.

Northern Analysis has identified lung, kidney, liver, ovary, adrenal gland, heart, pancreas, testis and brain as the tissues with the highest expression of the PY RNA. This mRMA distribution is consistent with the expression of other family members. All three other ligands have important functions in the central and peripheral nervous and endocrine system suggesting that PY is also an important player in that area, adding additional diversity of this family of peptides. PY has most likely evolved by gene duplication from the PYY gene probably in the same way as Seminal plasmin has in the bovine genome (6). Few mutations, however, have led to a different much shorter precursor.

The NPY family of peptides play a major role in a variety of important physiological functions like, regulation of blood pressure, anxiety, memory retention, hormone release and most interestingly food intake and it is to be expected that this novel family member contributes to this effects.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

SEQUENCE LISTING

<160> NUMBER OF SEQ ID NOS: 4

<210> SEQ ID NO 1
<211> LENGTH: 840
<212> TYPE: DNA
<213> ORGANISM: Homo sapiens

<400> SEQUENCE: 1

```
ccagtgcgcc cttgaaactt tcctcgcctt ccacctcctg ctcatctgct tcacaagctg      60
tcgctgtggt gtcggttcgc aggtcgtggc ctctcatggc cacggtgctt ttggccctgc     120
tcgtctacct gggggcgctg gtcgacgcct acccccatcaa acccgaggct cccggcgaag    180
acgccttcct ggggtagctg agccgctgct acgcctatcc tcgccactac ctcatcctgg    240
tcactcagcc gtcgtgagcg caggcgcggg gcgggcggac ggggacccct ggggctctcc    300
ccctacagcc ccgctccacc gggggcgtgg ctagatctga ccgcgcccgg ccaggccccg    360
ccctcaggta tgggaaacta ggccgcccag tcgcgcgcct ctccaaaacg ttcttcccag    420
actgcgagga ccgcctcggc aggtggcggt aaaagcgccc ccatcaagtc acataacatc    480
ctgcctccga gagcgcggtc tggcccccacc ctggtccatc atcacttacg acgtctccca    540
ggcttgcctc cccggatcgg attcctttcc cttcgatccc gcaggccgga gggcgcagac    600
ctgtggtgag gacacccgag gcctcctggg agacctgcag accacgccca cctcatttac    660
atgttcactc ccgaccctgg aaacccggat ttcgcctccg gacagcggcg tctgggcagg    720
gttcgggtac tgcagtcccg cgtctggatg ccccgcgccc cctgagctgc agggctgtgt    780
gtggtccttc cctggtccca aaataaagag cggattgcac agaaacggaa aaaaaaaaa     840
```

<210> SEQ ID NO 2
<211> LENGTH: 33
<212> TYPE: PRT
<213> ORGANISM: Homo sapiens

<400> SEQUENCE: 2

```
Met Ala Thr Val Leu Leu Ala Leu Leu Val Tyr Leu Gly Ala Leu Val
  1               5                  10                  15

Asp Ala Tyr Pro Ile Lys Pro Glu Ala Pro Gly Glu Asp Ala Phe Leu
             20                  25                  30

Gly
```

<210> SEQ ID NO 3
<211> LENGTH: 1110
<212> TYPE: DNA
<213> ORGANISM: Papio hamadryas

<400> SEQUENCE: 3

```
tccttgaaac tttcctcgcc ttctacctcc tgctcatctg cttcataagc tgtcgctgtg      60
agcggctggg ggctcaagca tggtctggta ccaggaaatc caggctgttt tgtcgggaaa     120
ctaaggctgg aatggtggaa gctcggggta agtggtgggg aactggattc gacggggtca     180
ttggaggtgg gaacgaggcc cgggactccc cgggagtccc cgttgccagc acaaccctct     240
tctctaattt acctctctgg cagcagcggt gccggggcgg tttatgtcag gcagggctta     300
tgtccctctg acagattagg aaactgaggc aggagccggt gcagtgccgg agaacacacg     360
gcaagttggt tgctgaacct tgatccgcta ccagcctcag ggagagggcc ggagcccggc     420
cagagggcag ccgcagcctc ctgccgtgga ggatcgaggc tcggaacgac ccacacccca     480
acgtcacctt cccagatggt gtcggtgcgc aggtcgtggc ctaccatggc cacagtgctt     540
ttggccctgc tcgtctacct gggggcgctg gtcgaggccc accccatcaa acccgaggct     600
ccaggcgaag acgccccct ggaggagctg agcctctact acgcctccct gagccactac     660
ctcaacctgg tcacccggcc gtggtgagcg caggcgcggg gtgggccgag cgggacccct     720
ggggctctcc cgctgcggcc cctctccacc gggggcgtgg tcagatttga ccacgccctt     780
ccaggcccca cccccaggca tgggaggaca gcccggacac acgcctctcc aaaacgttct     840
tcccagacgg cgaggaccgc ccgggcaggt cacagtaaaa gcgcccccgt caagtcacat     900
aacatcctgc ctccgagagt gcggcctggc cccaccctgg tacatcactt acgacgtctc     960
ccaggctcgc ctccccagat cggattcctt tcccttcact cccgcaggct ggaggcgcag    1020
acctgtggtg aggacccccg aggcctcctg ggagatctgc agaccacgcc cacctcattt    1080
acatgttcac tcccaatcac tagtgaattc                                     1110
```

<210> SEQ ID NO 4
<211> LENGTH: 63
<212> TYPE: PRT
<213> ORGANISM: Papio hamadryas

<400> SEQUENCE: 4

```
Met Val Ser Val Arg Arg Ser Trp Pro Thr Met Ala Thr Val Leu Leu
 1               5                  10                  15

Ala Leu Leu Val Tyr Leu Gly Ala Leu Val Glu Ala His Pro Ile Lys
            20                  25                  30

Pro Glu Ala Pro Gly Glu Asp Ala Pro Leu Glu Glu Leu Ser Leu Tyr
        35                  40                  45

Tyr Ala Ser Leu Ser His Tyr Leu Asn Leu Val Thr Arg Pro Trp
    50                  55                  60
```

References

1. Blomquist, A. G. & Hertzog. H. (1997) *Trends Neurosci* 7, 294–298.
2. Larhammar. D. *Regulatory Peptides* 62,1–11.
3. Leiter, A. B., Toder, A., Wolfe, H. J., Taylor, I. L., Cooperman, S., Mandel, G. & Goodman, R. H. (1987) *J. Biol. Chem.* 262. 12984–12988.
4. Taylor, I. L., Solomaon. T. E. Walsh, J & Grossman. M. I. (1979) *Gastroenterology* 76, 524–528.
5. Hort, Y. J., Baker. E., Sutherland, G., Shine, J. & Herzog, H. (1994) *Genomics*, 26, 77–83.
6. Herzog, H., Hort, Y., Schneider, R. and Shine, J. (1995) *Proc. Natl. Acad. Sci. USA* 92, 594–598.

What is claimed is:

1. An isolated PY peptide including an amino acid sequence characterized by amino acids 19 to 33 in SEQ ID NO:2.
2. An isolated PY peptide including an amino acid sequence as shown in SEQ ID NO:2.
3. A composition comprising a PY peptide according to claim 1 and a pharmaceutically acceptable carrier.
4. An isolated polynucleotide which encodes a human PY peptide comprising an amino acid sequence corresponding to amino acids 19 to 33 in SEQ ID NO:2.
5. An isolated polynucleotide comprising:
   (a) a sequence of nucleotides as show in SEQ ID NO:1
   (b) a sequence fully complimentary to the sequence of paragraph (a); or (c) a sequence which encodes a human PY peptide and which selectively hybridizes to a sequence in paragraph (b) under the following conditions:
hybridizing at 65° C. in a solution comprising 1.5× SSPE, 10% w/v polyethylene glycol 6000, 7% (w/v) SDS, 0.25 mg/ml fragmented herring sperm DNA; and
washing at 50° C. in a solution comprising 0.1×SSC and 0.1% (w/v) SDS.

6. A polynucleotide according to claim 5 which is less than 5000 nucleotides in length.

7. A polynucleotide according to claim 5 which is less than 2000 nucleotides in length.

8. A polynucleotide according to claim 5 which is less than 500 nucleotides in length.

9. An isolated polynucleotide comprising nucleotides 150 to 194 of SEQ ID NO:1.

10. An isolated polynucleotide encoding a PY peptide which has at least 90% homology with nucleotides 150–194 of SEQ IN NO:1.

11. An isolated polynucleotide encoding a PY peptide which has at least 95% homology with nucleotides 150–194 of SEQ ID NO:1.

12. A plasmid or expression vector including a polynucleotide according to claim 4.

13. A mammalian, insect, yeast, or bacterial host cell transformed with the polynucleotide according to claim 4.

14. A host cell according to claim 13 wherein the cell is a Chinese hamster ovary (CHO) cell, human embryonic kidney (HEK) 293 cell, a human VAtT 20 cell or an insect Sf9 cell.

15. A method of producing a PY peptide that includes culturing the host cell according to claim 13 under conditions enabling the expression of the polynucleotide.

16. An isolated polynucleotide encoding a PY peptide comprising an amino acid sequence as shown in SEQ ID NO:2.

17. The method of claim 15 that further includes recovering the expressed PY peptide.

* * * * *